(12) United States Patent
Koga et al.

(10) Patent No.: US 9,040,573 B2
(45) Date of Patent: May 26, 2015

(54) ANTI-FUNGAL AGENT

(71) Applicants: Hiroyasu Koga, Kawachinagano (JP);
Yasuko Nanjoh, Kawachinagano (JP);
Ryoji Tsuboi, Saitama (JP)

(72) Inventors: Hiroyasu Koga, Kawachinagano (JP);
Yasuko Nanjoh, Kawachinagano (JP);
Ryoji Tsuboi, Saitama (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 13/995,820

(22) PCT Filed: Sep. 25, 2012

(86) PCT No.: PCT/JP2012/074580
§ 371 (c)(1),
(2) Date: Aug. 13, 2013

(87) PCT Pub. No.: WO2013/047530
PCT Pub. Date: Apr. 4, 2013

(65) Prior Publication Data
US 2014/0142154 A1 May 22, 2014

(30) Foreign Application Priority Data

Sep. 26, 2011 (JP) ................. 2011-209903

(51) Int. Cl.
*A61K 31/4178* (2006.01)
*C07D 409/06* (2006.01)
(52) U.S. Cl.
CPC .......... *A61K 31/4178* (2013.01); *C07D 409/06* (2013.01)
(58) Field of Classification Search
USPC ........................................................ 514/397
See application file for complete search history.

(56) References Cited

U.S. PATENT DOCUMENTS

| 8,058,303 | B2 * | 11/2011 | Miki et al. ................. 514/397 |
| 8,492,421 | B2 | 7/2013 | Koga et al. |
| 2010/0249202 | A1 | 9/2010 | Koga et al. |
| 2013/0231379 | A1 | 9/2013 | Koga et al. |

OTHER PUBLICATIONS

Koga (In vitro antifungal activity of luliconazole against clinical isolates from patients with dermatomycoses, Jounal Infect Chemother, 2006, 12: pp. 163-165).*
Abe et al., "Anti-Candida Activities of Azole Antifungals in the Presence of Lysozyme In Vitro," *Japanese Journal of Medical Mycology*, 39(2): 103-107 (1998).
Elewski et al., "*Hendersonula toruloidea* and *Scytalidium hyalinum*," *Archives of Dermatology*, 127: 1041-1044 (Jul. 1991).
Greer et al., "Tinea pedis caused by *Hendersonula toruloidea*," *Journal of the American Academy of Dermatology*, 16(5): 1111-1115 (May 1987).

Guarro et al., "In vitro antifungal susceptibility of nondermatophytic keratinophilic fungi," *Biology of Dermatophytes and Other Keratinophilic Fungi* [*Antifungal Susceptibilities of Scytalidium and Chrysosporium*] (Revista Iberoamericana de Micoloia, Bilbao, Spain), 142-147 (2000).
Lacroix et al., "In vitro activity of amphotericin B, itraconazole, voriconazole, posaconazole, caspofungin and terbinafine against *Scytalidium dimidiatum* and *Scytalidium hyalinum* clinical isolates," *Journal of Antimicrobial Chemotherapy*, 61(4): 835-837 (Apr. 2008).
Moore, Mary, "*Hendersonula toruloidea* and *Scytalidium hyalinum* infections in London, England," *Journal of Medical and Veterinary Mycology*, 24: 219-230 (1986).
Moore et al., "*Scytalidium hyalinum* infection diagnosed in Spain," *Journal of Medical and Veterinary Mycology*, 22: 243-245 (1984).
Morris-Jones et al., "*Scytalidium dimidiatum* Causing Recalcitrant Subcutaneous Lesions Produces Melanin," *Journal of Clinical Microbiology*, 42(8): 3789-3794 (Aug. 2004).
Nanjoh et al., "In Vitro Antifungal Activities of Clinically Available Topical Antifungal Drugs," *Japanese Journal of Dermatology*, 117(2): 149-152 (Feb. 20, 2007).
Niwano et al., "Efficacy of NND-502, a novel imidazole antimycotic agent, in experimental models of *Candida albicans* and *Aspergillus fumigatus* infections," *International Journal of Antimicrobial Agents*, 12(3): 221-228 (1999).
Summerbell et al., "Onychomycosis, Tinea Pedis and Tinea Manuum Caused by Non-Dermatophytic Filamentous Fungi," *Mycoses*, 32(8): 609-619 (1989).
Ungpakorn, Rataporn, "Mycoses in Thailand: Current Concerns," *Japanese Journal of Medical Mycology*, 46: 81-86 (2005).
Ungpakorn, Rataporn, "Nondermatophyte infections of the skin and nails: Implications for therapy," *The 17th Congress of The International Society for Human and Animal Mycology* (ISHAM 2009, Tokyo, Japan), Program and Abstract Book, item CL-08-3 (May 25-29, 2009).
Yamaguchi, Hideyo, *Pathogenic Fungi and Mycoses*, Revised 4th Edition: 148-149 (2007).
Japanese Patent Office, International Search Report in International Patent Application No. PCT/2012/074580 (Nov. 6, 2012).
Japanese Patent Office, Written Opinion of the International Search Authority in International Patent Application No. PCT/2012/074580 Nov. 6, 2012.
Koga et al., "In vitro antifungal activities of luliconazole, a new topical imidazole," *Medical Mycology*, 47: 640-647 (Sep. 2009).
Lacroix et al., "In vitro activity of amphotericin B, itraconazole, voriconazole, posaconazole, caspofungin and terbinafine against *Scytalidium dimidiatum* and *Scytalidium hyalinum* clinical isolates," *Journal of Antimicrobial Chemotherapy*, 61: 835-837 (2008).
Morris-Jones et al., "*Scytalidium dimidiatum* Causing Recalcitrant Subcutaneous Lesions Produces Melanin," *Journal of Clinical Microbiology*, 42: 3789-3794 (Aug. 2004).

* cited by examiner

*Primary Examiner* — Kathrien Cruz
(74) *Attorney, Agent, or Firm* — Leydig, Voit & Mayer, Ltd.

(57) ABSTRACT

An antifungal agent against a fungus of the genus *Scytalidium* (*Scytalidium_dimidiatum*, *Scytalidium_hyalinum* etc.), preferably an antifungal agent for superficial mycosis caused by a fungus of the genus *Scytalidium* as a pathogenic fungus, which contains luliconazole or a pharmaceutically acceptable salt thereof and/or lanoconazole or a pharmaceutically acceptable salt thereof as active ingredient(s).

10 Claims, No Drawings

ANTI-FUNGAL AGENT

CROSS-REFERENCE TO RELATED APPLICATIONS

This patent application is the U.S. national phase of International Patent Application No. PCT/JP2012/074580, filed Sep. 25, 2012, which claims the benefit of Japanese Patent Application No. 2011-209903, filed on Sep. 26, 2011, which are incorporated by reference in their entireties herein.

TECHNICAL FIELD

The present invention relates to an antifungal agent against the genus *Scytalidium*, particularly an antifungal agent having an effect of prophylaxis, treatment, cure, alleviation of symptoms, prevention of recurrence and the like against mycosis (particularly superficial mycosis) caused by said pathogenic fungus, which contains luliconazole or a pharmaceutically acceptable salt thereof and/or lanoconazole or a pharmaceutically acceptable salt thereof as active ingredient(s).

TECHNICAL BACKGROUND

Superficial mycosis is defined as a disease wherein the pathogen is localized in a keratinized tissue such as epidermis, hair, nail and the like, and a mucosal area adjacent to the skin such as mouth cavity, vagina and the like, and is a disease developed most frequently. As antifungal agents conventionally used for the treatment of mycosis, azole antifungal agents (luliconazole, lanoconazole, bifonazole, ketoconazole, miconazole, itraconazole, clotrimazole, neticonazole, oxiconazole, tioconazole, croconazole, omoconazole, sulconazole and salts thereof etc.); benzylamine antifungal agents (butenafine and a salt thereof etc.); allylamine antifungal agents (terbinafine and a salt thereof etc.); morpholine antifungal agents (amorolfine and a salt thereof etc.); thiocarbamic acid antifungal agents (liranaftate, tolnaftate, tolciclate etc.); and antibiotics (nystatin, trichomycin, variotin, siccanin, pyrrolnitrin, amphotericin etc.) and the like are known. While the species and drug sensitivity of pathogenic fungus to be the target of these antifungal agents vary depending on each antifungal agent, the pathogenic fungus includes genus *Candida*, genus *Cryptococcus*, genus *Aspergillus*, genus *Trichophyton*, genus *Malassezia*, genus *Coccidioides* and the like (see non-patent document 1).

Recently, however, intractable superficial mycosis in each country of South East Asia (particularly, Thailand), North America and Europe has been reported (see non-patent documents 2, 6, 7, 9, 10 and 11). In addition, it has been reported in the International Society for Human and Animal Mycology (ISHAM-2009) that said pathogenic fungus is derived from a fungus of the genus *Scytalidium* (*Scytalidium dimidiatum* etc.) (see non-patent documents 3 and 8). Furthermore, commercially available drugs including an azole antifungal agent have been reported to show a low activity against fungus of the genus *Scytalidium* (*Scytalidium dimidiatum* etc.) (see non-patent document 4 or 5), and a risk of failing effective treatment when pandemic occurs in Japan or in the world has been indicated (see non-patent document 3).

DOCUMENT LIST

Non-Patent Documents non-patent document 1: Byougensinkin to Sinkinshou (Pathogenic Fungus and Mycosis), Revised 4th Edition, NANZANDO Co., Ltd.
non-patent document 2: JAPAN JOURNAL MEDICINAL MYCOLOGY, Vol. 46, 81-86, 2005
non-patent document 3: THE 17TH CONGRESS OF THE INTERNATIONAL SOCIETY FOR HUMAN AND ANIMAL MYCOLOGY 2009 PROGRAM AND ABSTRACT BOOK CL-08-3
non-patent document 4: JOURNAL OF ANTIMICROBIAL CHEMOTHERAPY (2008) 61, 835-837
non-patent document 5: Biology of Dermatophytes and other Keratinophilic Fungi (Revista Iberoamericana de Micoloia, Bilbao, 2000. 142-147)
non-patent document 6: Journal of the American Academy of Dermatogy (1987) 16, 1111-1115
non-patent document 7: Arch. Dermatol., Vol. 127, July, 1991, 1041-1044
non-patent document 8: Journal of Clinical Microbiology, August 2004, 3789-3794
non-patent document 9: Mycoses, 32 (8) 609-619, 1989
non-patent document 10: Journal of Medical and Veterinary Mycology (1986) 24, 219-230
non-patent document 11: Journal of Medical and Veterinary Mycology (1984) 22, 243-245

SUMMARY OF THE INVENTION

Problems to be Solved by the Invention

The problem of the present invention is to find out a substance showing a strong antifungal activity against a fungus of the genus *Scytalidium* (*Scytalidium dimidiatum* etc.), and provide an antifungal agent effective even for intractable superficial mycosis caused by the pathogenic fungus of the genus *Scytalidium*.

Means of Solving the Invention

In view of the aforementioned reports of the International Society for Human and Animal Mycology and the like, the present inventors have conducted intensive studies of a medicament effective for a fungus of the genus *Scytalidium* (*Scytalidium dimidiatum* etc.) which is the pathogen of intractable superficial mycosis, and surprisingly found that luliconazole and lanoconazole from among the azole antifungal agents considered to afford a low effect have an extremely strong antifungal activity against a fungus of the genus *Scytalidium*, and that they are extremely highly effective as therapeutic agents for superficial mycosis caused by a fungus of the genus *Scytalidium*, which resulted in the completion of the present invention.

Accordingly, the present invention relates to
[1] an antifungal agent against a fungus of the genus *Scytalidium*, comprising luliconazole or a pharmaceutically acceptable salt thereof and/or lanoconazole or a pharmaceutically acceptable salt thereof as active ingredient(s);
[2] an antifungal agent for mycosis caused by a fungus of the genus *Scytalidium* as a pathogenic fungus, which comprises luliconazole or a pharmaceutically acceptable salt thereof and/or lanoconazole or a pharmaceutically acceptable salt thereof as active ingredient(s);
[3] the antifungal agent of the above-mentioned [2], wherein the mycosis is selected from superficial mycosis, subcutaneous mycosis, deep mycosis, mycetoma and fungemia;
[4] the antifungal agent of the above-mentioned [3], wherein the mycosis is superficial mycosis;
[5] the antifungal agent of the above-mentioned [4], wherein the superficial mycosis is a mycosis developed by infection, with the pathogen, of the skin of leg, body and/or head, nail, eye, ear, mouth cavity, nasal cavity, respiratory organ, urinary tract and/or vagina;

[6] the antifungal agent of any of the above-mentioned [1] to [5], wherein the fungus of the genus *Scytalidium* is *Scytalidium dimidiatum* and/or *Scytalidium hyalinum*;

[7] a method of treating mycosis caused by a fungus of the genus *Scytalidium* as a pathogenic fungus, comprising administering an effective amount of luliconazole or a pharmaceutically acceptable salt thereof and/or lanoconazole or a pharmaceutically acceptable salt thereof to a subject;

[8] the method of the above-mentioned [7], wherein the mycosis is superficial mycosis;

[9] use of luliconazole or a pharmaceutically acceptable salt thereof and/or lanoconazole or a pharmaceutically acceptable salt thereof for the production of an antifungal agent for mycosis caused by a fungus of the genus *Scytalidium* as a pathogenic fungus;

[10] the use of the above-mentioned [9], wherein the mycosis is superficial mycosis;

[11] luliconazole or a pharmaceutically acceptable salt thereof and/or lanoconazole or a pharmaceutically acceptable salt thereof for use in the treatment of mycosis caused by a fungus of the genus *Scytalidium* as a pathogenic fungus;

[12] the compound of the above-mentioned [11], wherein the mycosis is superficial mycosis;

[13] an antifungal agent for complex mycosis caused by (1) a fungus of the genus *Scytalidium* and (2) one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium* as pathogenic fungi, which comprises luliconazole or a pharmaceutically acceptable salt thereof and/or lanoconazole or a pharmaceutically acceptable salt thereof as active ingredient(s);

[14] the antifungal agent of the above-mentioned [13], wherein the complex mycosis is selected from superficial mycosis, subcutaneous mycosis, deep mycosis, mycetoma and fungemia;

[15] the antifungal agent of the above-mentioned [14], wherein the complex mycosis is superficial mycosis;

[16] the antifungal agent of the above-mentioned [15], wherein the superficial mycosis is a mycosis developed by infection, with the pathogen, of the skin of leg, body and/or head, nail, eye, ear, mouth cavity, nasal cavity, respiratory organ, urinary tract and/or vagina;

[17] a method of treating complex mycosis caused by
(1) a fungus of the genus *Scytalidium* and
(2) one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium*
as pathogenic fungi,
which comprises administering an effective amount of luliconazole or a pharmaceutically acceptable salt thereof and/or lanoconazole or a pharmaceutically acceptable salt thereof to a subject;

[18] the method of the above-mentioned [17], wherein the complex mycosis is superficial mycosis;

[19] use of luliconazole or a pharmaceutically acceptable salt thereof and/or lanoconazole or a pharmaceutically acceptable salt thereof for the production of an antifungal agent for complex mycosis caused by
(1) a fungus of the genus *Scytalidium* and
(2) one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium* as pathogenic fungi;

[20] the use of the above-mentioned [19], wherein the complex mycosis is superficial mycosis;

[21] luliconazole or a pharmaceutically acceptable salt thereof and/or lanoconazole or a pharmaceutically acceptable salt thereof for use in the treatment of complex mycosis caused by
(1) a fungus of the genus *Scytalidium* and
(2) one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium*
as pathogenic fungi;

[22] the compound of the above-mentioned [21], wherein the complex mycosis is superficial mycosis;
and the like.

Effect of the Invention

The antifungal agent of the present invention is characterized in that it has a high antifungal effect against a fungus of the genus *Scytalidium* (*Scytalidium dimidiatum* etc.), and provides a high treatment effect on mycosis caused by the pathogenic fungus of the genus *Scytalidium*, particularly superficial mycosis. In addition, the antifungal agent of the present invention characteristically causes low irritation to the inflammatory skin and is easily applied.

DESCRIPTION OF EMBODIMENTS

While the active ingredient used for the antifungal agent of the present invention is luliconazole; (−)-(E)-[(4R)-(2,4-dichlorophenyl)-1,3-dithioran-2-ylidene](1H-imidazol-1-yl) acetonitrile (see JP-A-H09-100279), and/or lanoconazole; [4-(2-chlorophenyl)-1,3-dithioran-2-ylidene](1H-imidazol-1-yl)acetonitrile (see JP-B-H03-24448), they/it may be a salt form. The salt is preferably a pharmaceutically acceptable salt. Examples of the pharmaceutically acceptable salt include salts with inorganic acid such as hydrochloric acid, hydrobromic acid, nitric acid, sulfuric acid, phosphoric acid and the like, salts with organic acid such as acetic acid, phthalic acid, fumaric acid, oxalic acid, tartaric acid, maleic acid, citric acid, succinic acid, methanesulfonic acid, p-toluenesulfonic acid and the like.

Each of luliconazole and lanoconazole may be used alone or they may be used in a mixture. The mixing ratio when used in a mixture is not particularly limited and may be an optional ratio. The amount of the active ingredient to be blended is 0.05 mass % to 5 mass % of the total amount of the antifungal agent. In addition, luliconazole and lanoconazole are characteristically free of skin irritation, cause low irritation to the inflammatory skin, and are easily applied.

The antifungal agent of the present invention may further contain antifungal agents other than luliconazole and lanoconazole. Examples of other antifungal agent include azole antifungal agents such as bifonazole, ketoconazole, miconazole, itraconazole, clotrimazole, neticonazole, oxiconazole, tioconazole, croconazole, omoconazole, sulconazole and salts thereof and the like; benzylamine antifungal agents such as butenafine and a salt thereof and the like; allylamine antifungal agents such as terbinafine and a salt thereof and the like; morpholine antifungal agents such as amorolfine and a salt thereof and the like; thiocarbamic acid antifungal agents such as liranaftate, tolnaftate and tolciclate and the like; antibiotics such as nystatin, trichomycin, variotin, siccanin, pyrrolnitrin, amphotericin etc., and the like.

The amount of other antifungal agent to be added is not particularly limited, and it may be added to luliconazole and/or lanoconazole at any ratio.

The mycosis to be the target of use of the antifungal agent of the present invention is not particularly limited as long as the pathogen thereof is a fungus of the genus *Scytalidium*. Examples thereof include superficial mycosis, subcutaneous mycosis, deep mycosis, mycetoma and fungemia, preferably superficial mycosis caused by a fungus of the genus *Scytalidium* as a pathogen. The superficial mycosis is specifically a disease state wherein the skin of leg, body and/or head, nail, eye, ear, mouth cavity, nasal cavity, respiratory organ, urinary tract and/or vagina and the like are infected with a fungus as a pathogen, and inflammation and the like are developed in the affected part.

While the fungus of the genus *Scytalidium* to be the pathogen is not particularly limited, specific examples thereof include *Scytalidium dimidiatum, Scytalidium hyalinum, Scytalidium lignicola* and the like. Particularly important as the pathogenic fungus is *Scytalidium dimidiatum* and *Scytalidium hyalinum*. *Scytalidium dimidiatum* is also called *Neoscytalidium dimidiatum* or *Hendersonula toruloidea*.

In addition, the mycosis to be the target of application of the antifungal agent of the present invention also includes complex mycosis showing complex infection with fungus other than genus *Scytalidium*, for example, one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, a fungus of the genus *Acremonium* and the like as pathogen(s), in addition to the aforementioned fungus of the genus *Scytalidium*. Particularly, the agent also shows effect for superficial complex mycosis.

The antifungal activity of luliconazole and lanoconazole against a fungus of the genus *Candida*, a fungus of the genus *Cryptococcus*, a fungus of the genus *Aspergillus*, a fungus of the genus *Trichophyton*, a fungus of the genus *Malassezia*, a fungus of the genus *Coccidioides*, a fungus of the *Zygomycota*, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium* is described in, for example, Journal of Infection and Chemotherapy, 2004, 10(4), 216-216, The Japanese Journal of Antibiotics, 1995, 48(1), 146-149, Japanese Journal of Medical Mycology, 2006, 47, 299-304, The Japanese Journal of Antibiotics, 1995, 48(1), 140-145, Japanese Journal of Medical Mycology, 1992, 3, 217-220, International Journal of Antimicrobial Agents, 2003, 21(3), 234-238 and the like.

The antifungal agent of the present invention can be administered to a treatment subject, for example, mammals (e.g., human, mouse, rat, hamster, rabbit, cat, dog, bovine, sheep, monkey etc.) in any route of oral and parenteral administrations (e.g., intravenous injection, muscular injection, subcutaneous administration, rectal administration, transdermal administration), preferably transdermal administration. Particularly preferably, the antifungal agent of the present invention is applied to a affected part of the skin of a treatment subject affected with superficial mycosis. Where necessary, it may be further covered with a bandage, film and the like. The dose may be any as long as it is an amount permitting uniform application of a therapeutic agent for superficial mycosis, which contains a predetermined concentration of the active ingredient, to a affected part of the skin.

When the antifungal agent of the present invention is transdermally administered, an oily base, an emulsifier and an emulsion stabilizer, solubilizing agent, powder component, polymer component, adhesion improver, film former, pH adjuster, antioxidant, antiseptic, preservative, agent for maintaining shape, moisturizing agent, skin protector, algefacient, flavor, colorant, chelating agent, lubricant, stratum corneum softening agent, blood circulation promoter, astringent, tissue repair promoter, antiperspirant, plant extraction component, animal extraction component and the like can be added as necessary besides the above-mentioned active ingredients.

Examples of the oily base include higher alcohols such as oleyl alcohol, stearyl alcohol, cetostearyl alcohol, cetanol, benzyl alcohol and the like, fatty acid esters such as ethyl acetate, isopropyl acetate, butyl acetate, diisopropyl adipate, diethyl sebacate, isopropyl myristate, octyldodecyl oleate, octyldodecyl myristate, isostearyl myristate, lanolin and the like, medium-chain triglycerides such as beef fat, olive oil and the like, fatty acid such as squalene, squalane and the like, jojoba oil, cetaceum, white petrolatum, liquid paraffin, microcrystalline wax, terpenes such as l-menthol, d-camphor, cineol, geraniol, limonene, pulegone, thymol, aphidicolin, forskolin, phytanic acid, phytol and the like, carboxylates of terpenoids such as menthyl lactate and the like, crotamiton, esters such as diethyl ether, isopropyl ether, tetrahydrofuran, dioxane, 2-methoxyethanol, 1,2-dimethoxyethane, etc. and the like.

Examples of the emulsifier include polyoxyethylene hydrogenated castor oil, sorbitan monostearate, sorbitan monopalmitate, glyceryl monostearate, sorbitan monolaurate, polyoxyethylene-polyoxypropylene block copolymer, polysorbates (polysorbates are fatty acid polyoxyethylene sorbitan different in the kind of fatty acid, and examples include polysorbate 60 (alias name: polyoxyethylene sorbitan monostearate (20E.O.)), polysorbate 40, Tween 40, polyoxyethylene sorbitan monopalmitate and the like), sodium lauryl sulfate, sucrose ester of fatty acid, lecithin and the like.

Examples of the solubilizing agent include water-soluble components capable of dissolving poorly water-soluble components. Examples of the component include polyvalent alcohols such as propylene glycol, 1,3-butylene glycol, glycerol and the like, low-molecular ketones such as methyl ethyl ketone, cyclohexanone and the like, macrogols and the like.

Examples of the emulsion stabilizer include higher alcohols such as cetostearyl alcohol and the like, acrylic acid polymer, carboxyvinyl polymer, polysaccharides such as xanthan gum, etc. and the like, which have a thickening effect, a film forming effect, an adhesion improving effect, and other effects.

Examples of the organic and inorganic powder components include zinc oxide, titanium oxide, magnesium stearate, talc, magnesium carbonate, magnesium oxide, silicic anhydride, silicic hydride, magnesium silicate, kaolin, AEROSIL, acid clay, mica, cornstarch, aluminum metasilicate and the like.

Examples of the polymer component include acrylic acid polymer, carboxyvinyl polymer, polysaccharides such as xanthan gum and the like, polypeptides and the like.

Examples of the adhesion improver include higher alcohols such as cetostearyl alcohol and the like, acrylic acid polymer, carboxyvinyl polymer, polysaccharides such as xanthan gum and the like, polypeptides and the like.

Examples of the film forming agent include higher alcohols such as cetostearyl alcohol and the like, acrylic acid polymer, carboxyvinyl polymer, polysaccharides such as xanthan gum and the like, polypeptides, collodion, polyvinylpyrrolidone, polyvinyl alcohol, celluloses such as nitrocellulose, etc. and the like.

Examples of the pH adjuster include organic acids such as citric acid, lactic acid, tartaric acid, stearic acid, palmitic acid, oleic acid and the like, organic acid salts such as sodium pyrophosphate and the like, inorganic bases such as sodium hydroxide and the like, organic amines such as diisopropanolamine, triethanolamine, etc. and the like.

Examples of the antioxidant include dibutylhydroxytoluene (BHT), butylhydroxyanisole (BHA), α-tocopherol, erythorbic acid, sodium pyrosulfite, sodium ascorbate and the like. Examples of the stabilizer include EDTA-2Na and the like.

Examples of the antiseptic or preservative include parabens such as methylparaben and the like, benzyl alcohol, sodium dehydroacetate, sorbic acid and the like.

Examples of the agent for maintaining shape include plant-derived dextrin saccharose ester and the like. Examples of the moisturizing agent include saccharides such as sodium hyaluronate, sodium chondroitin sulfate, glycosyl trehalose, xylitol, sorbitol and the like, proteins and amino acids such as collagen, arginine, hydrolyzed silk, Sericin and the like, sodium lactate, the below-mentioned plant extraction components and the like.

Examples of the skin protector include vitamin derivatives such as sodium riboflavin phosphate, magnesium ascorbyl phosphate, cyanocobalamin and the like, polyphenols such as glucosylrutin and the like, hydroxyproline or derivatives thereof such as hydroxyproline, dipalmitoyl hydroxyproline and the like, ceramide, aminocaproic acid, siloxane derivatives such as stearoxy methylpolysiloxane, trimethylsiloxysilicate and the like, glycolipids such as cerebrosides, etc. and the like.

Examples of the algefacient include mint (l-menthol), camphor, ethanol, eucalyptus oil and the like. The colorant is not particularly limited and, for example, Red No. 202, iron oxide and the like can be mentioned. Examples of the chelating agent include EDTA-2Na (edetate), tetrasodium etidronate, pentasodium triphosphate, pentasodium pentetate and the like. Examples of the lubricant include silica, calcium stearate, magnesium stearate and the like.

Stratum corneum softening agents such as urea, organic acid esters (diethyl phthalate etc.), organic acids (lactic acid etc.), fats and oils (cetaceum, cholesterol etc.) and the like can also be added. Examples of the blood circulation promoter include benzyl nicotine, heparinoid, chili pepper and the like. Examples of the astringent include aluminum chloride, aldioxa and the like. Examples of the tissue repair promoter include aluminum chlorohydroxy allantoinate, lysozyme chloride and the like. Examples of the antiperspirant include inorganic salt and organic salt or complex and a mixture thereof and the like of aluminum, zirconium or zinc such as aluminum salt, zirconium salt and the like (e.g., aluminum halide, hydroxylaluminum halide, zirconium oxyhalide, hydroxyzirconium halide, and a mixture thereof), citric acid, lactic acid, kojic acid, menthol and the like.

Examples of the plant extraction component include aloe extract, *Scutellaria baicalensis* root extract, mulberry extract, *Prunus persica* leaf extract, *Gardenia florida* leaf extract, *Eleutherococcus* extract, *Phellodendron* bark extract, *Hypericum perforatum* extract, rice polishing extract, green tea extract, licorice extract, algae extract, clove extract, Japanese angelica root extract, chili pepper extract, rosemary leaf oil and the like. Examples of the animal extract component etc. include plant worm extract, royal jelly extract and the like.

As these pharmaceutically acceptable additives for pharmaceutical products or cosmetics etc., those generally used for preparations can be used.

The antifungal agent of the present invention can be formulated using the above-mentioned components other than the active ingredient and the like into an external drug such as cream, liquid, lotion, emulsion, tincture, ointment, aqueous gel, oily gel, aerosol, powder, shampoo, soap, enamel for coating nail and the like by a method conventionally used in the field of pharmaceutical preparations.

In addition, other anti-inflammatory agents and the like can also be added as an active ingredient to suppress inflammatory conditions. Examples of such anti-inflammatory agent and antipruritic agent include sapogenins such as crotamiton, glycyrrhizinate, oleanolic acid and the like, antihistamine agents such as diphenhydramine, chlorpheniramine, chlorpheniramine maleate, dimenhydrinate, promethazine and the like, topical anesthetics such as lidocain, dibucaine, procaine, ethyl aminobenzoate and a salt thereof and the like, allantoin, oxipolyethoxydodecan and the like.

When the antifungal agent of the present invention is orally administered, it can be prepared in the dosage form suitable for oral administration, such as capsule, tablet, granule, powder, pill, fine granule, troche and the like. These preparations can be produced by a conventional method by using additives generally used for oral preparations such as excipient, extender, binder, wetter, disintegrant, surfactant, lubricant, dispersing agent, buffering agent, preservative, solubilizing agents, preservative, flavor, soothing agent, stabilizer and the like. Examples of usable additives include lactose, fructose, glucose, starch, gelatin, methylcellulose, gum arabic, polyethylene glycol, citric acid, sodium sulfite, sodium phosphate, β-cyclodextrin, hydroxypropyl-β-cyclodextrin and the like. While the dose is appropriately determined in consideration of the usage, age, sex and level of symptom of the treatment subject, and the like, it is generally, for example, about 1 to 2000 mg, preferably 10 to 1000 mg, per day for an adult, which can be administered once or in several portions per day.

EXAMPLES

While specific preparations and antifungal activity tests of the antifungal agent of the present invention are given as examples below, the present invention is not limited thereto.

The "amount (mass %)" in the present specification means mass percentage to the total amount of the composition, unless otherwise specified.

Formulation Example 1

Cream Formulation Example

| luliconazole | 50 g |
| cetostearyl alcohol | 1,000 g |
| diethyl sebacate | 600 g |
| medium-chain triglyceride | 800 g |
| polysorbate 60 | 400 g |
| sorbitan monostearate | 200 g |
| methylparaben | 15 g |
| propylparaben | 5 g |
| benzyl alcohol | 100 g |
| dibutylhydroxytoluene | 2 g |
| purified water | balance |
| total | 10,000 g |

Of the above-mentioned components, the oil phase components (luliconazole, cetostearyl alcohol, diethyl sebacate, medium-chain triglyceride, polysorbate 60, sorbitan monostearate, propylparaben, benzyl alcohol and dibutylhydroxytoluene) were mixed with heating, cooled, and the aqueous phase components (methylparaben and purified water) were added with stirring to produce a cream (10,000 g).

Formulation Example 2

Liquid Formulation Example

| lanoconazole | 100 g |
| macrogol 400 | 3,300 g |
| methylethyl ketone | 1,000 ml |
| ethanol | 4,500 ml |
| purified water | balance |
| total | 10,000 ml |

The above-mentioned respective components were mixed and dissolved to produce a liquid (10,000 mL).
Antifungal Activity Test 1
Strain Used

*Scytalidium dimidiatum* strain of clinical isolate obtained by separation and identification from nail or stratum corneum of patients with superficial mycosis was used. The fungi pre-cultured on an SDA medium was suspended in 0.1% (w/v) Tween 80-containing sterile saline and the suspension was filtered through gauze to collect arthrospore. This was suspended in 0.1% (w/v) Tween 80-containing sterile saline, and added to a 20% Alamar Blue-containing medium to $2\times10^4$ cells/mL to give a fungal inoculum solution.
Drugs Used Luliconazole (LLCZ), lanoconazole (LCZ), bifonazole (BFZ), ketoconazole (KCZ), miconazole (MCZ), clotrimazole (CTZ), itraconazole (ITZ), voriconazole (VCZ), fluconazole (FCZ), terbinafine (TBF), amorolfine (AMO), and amphotericin B (AMPB).

Each drug was used after dissolving in DMSO (dimethyl sulfoxide).
Test Method

The minimum inhibitory concentration (MIC) was measured by a broth microdilution method. That is, RPMI1640 medium (Sigma-Aldrich) was buffered with 0.165 M morpholine propanesulfonic acid (MOPS, Wako Pure Chemical Industries, Ltd.) to pH 7.0, and a given amount of a solution of the drug in DMSO was added thereto to prepare 2-fold dilution series within the range of 0.00098-4 µg/mL. This was added to a 96-well microplate by 100 µL, a fungal inoculum solution (100 µL, final concentration of fungi to be added: $1.0\times10^4$ cells/mL) was added, and the mixture was cultured at 35° C. An Alamar Blue reagent was added in advance to the culture medium (final addition concentration: 10%) and, at the time point when the Alamar Blue reagent in the drug-free growth control group changed from blue to red, the culture was discontinued and the absorbance (differential optical density at 570 nm based on 590 nm served as reference) measured. The minimum concentration of the drug that inhibited the growth of the fungus in the growth control group by 80% or more was taken as MIC. The concentration to be MIC ($MIC_{90}$) in 9 strains out of the 10 strains (90%) measured was determined.

Reference documents for measurement method: Takako Shinoda et al.: opinion proposed by Committee for Clinical Laboratory Standards of The Japanese Society for Medical Mycology (1995-1997), Method for antifungal susceptibility testing of filamentous fungus, Medical Mycology Journal, 40: 239-257, 1999.

Clinical Laboratory Standards Institute/National Committee for Clinical Laboratory Standards. Reference method for broth dilution antifungal susceptibility testing of filamentous fungus. Approved Standard M38-A2. Wayne, Pa.: National Committee for Clinical Laboratory Standards, 2008.
Test Results The MICs of various drugs against *Scytalidium dimidiatum* are shown in Table 1. Luliconazole and lanoconazole showed a specifically strong antifungal activity as compared to other drugs, and $MIC_{90}$ thereof was as extremely low as 0.002 and 0.0039 µg/mL, respectively.

TABLE 1

| clinical isolate | MIC (µg/mL) | | | | | | | | | | | |
| --- | --- | --- | --- | --- | --- | --- | --- | --- | --- | --- | --- | --- |
| | LLCZ | LCZ | BFZ | KCZ | MCZ | CTZ | ITZ | VCZ | FCZ | TBF | AMO | AMPB |
| 530999 | 0.002 | 0.002 | 0.13 | >4 | 0.5 | 0.25 | >4 | 0.13 | >4 | 0.5 | 1 | 0.5 |
| 530129 | 0.002 | 0.0039 | 0.25 | 4 | 1 | 0.5 | >4 | 0.25 | >4 | 0.5 | 0.5 | 0.25 |
| 530251 | 0.002 | 0.0039 | 0.25 | >4 | 1 | 0.25 | >4 | 0.13 | >4 | 0.5 | 2 | 0.25 |
| 531581 | 0.002 | 0.0039 | 0.25 | >4 | 0.5 | 0.25 | >4 | 0.25 | >4 | 0.5 | 0.5 | 0.25 |
| 530946 | 0.002 | 0.0039 | 0.25 | >4 | 1 | 0.5 | >4 | 0.25 | >4 | 1 | 1 | 0.25 |
| 531869 | 0.00098 | 0.002 | 0.13 | 2 | 0.5 | 0.25 | >4 | 0.13 | >4 | 0.5 | 0.5 | 0.25 |
| 530621 | 0.002 | 0.0039 | 0.25 | >4 | 1 | 0.5 | >4 | 0.25 | >4 | 0.5 | 1 | 0.25 |
| 530633 | 0.002 | 0.0039 | 0.13 | 4 | 0.5 | 0.5 | >4 | 0.25 | >4 | 0.25 | 0.5 | 0.25 |
| 530142 | 0.002 | 0.002 | 0.13 | >4 | 1 | 0.5 | >4 | 0.25 | >4 | 0.25 | 1 | 0.13 |

TABLE 1-continued

| clinical isolate | MIC (µg/mL) | | | | | | | | | | | |
|---|---|---|---|---|---|---|---|---|---|---|---|---|
| | LLCZ | LCZ | BFZ | KCZ | MCZ | CTZ | ITZ | VCZ | FCZ | TBF | AMO | AMPB |
| 530914 | 0.002 | 0.0039 | 0.13 | >4 | 1 | 0.5 | >4 | 0.25 | >4 | 0.25 | 2 | 0.13 |
| $MIC_{90}$ | 0.002 | 0.0039 | 0.25 | >4 | 1 | 0.5 | >4 | 0.25 | >4 | 0.5 | 2 | 0.25 |

LLCZ: luliconazole,
LCZ: lanoconazole,
BFZ: bifonazole,
KCZ: ketoconazole,
MCZ: miconazole,
CTZ: clotrimazole,
ITZ: itraconazole,
VCZ: voriconazole,
FCZ: fluconazole,
TBF: terbinafine,
AMO: amorolfine,
AMPB: amphotericin B Antifungal Activity Test 2
Strain Used

*Scytalidium hyalinum* strain of clinical isolate available from CBS (Netherlands) was used. The fungus was pre-cultured in an SDA medium, 0.1% (w/v) Tween 80-containing sterile saline was added to give a suspension, which was filtered through gauze to collect arthrospore. This was suspended in 0.1% (w/v) Tween 80-containing sterile saline, and added to a 20% Alamar Blue-containing medium to $2 \times 10^4$ cells/mL to give a fungal inoculum solution.

Drugs Used luliconazole (LLCZ), lanoconazole (LCZ), voriconazole (VCZ), amphotericin B (AMPB), itraconazole (ITZ), fluconazole (FCZ), bifonazole (BFZ), clotrimazole (CTZ), ketoconazole (KCZ), miconazole (MCZ), terbinafine (TBF), and amorolfine (AMO).

Each drug was used after dissolving in DMSO (dimethyl sulfoxide).

The test method was the same as in the aforementioned antifungal activity test 1, and the minimum concentration of the drug that inhibited the growth of the fungus in the growth control group by 80% or more was taken as MIC. The MIC range of the 4 strains measured and the geometric mean (GM) of each drug were determined.

Test Results

The MICs of various drugs against *Scytalidium hyalinum* are shown in Table 2. Luliconazole and lanoconazole showed a specifically strong antifungal activity as compared to other drugs, and GM thereof was as extremely low as 0.00058 and 0.00098 µg/mL, respectively.

TABLE 2

| clinical isolate | MIC (µg/mL) | | | | | |
|---|---|---|---|---|---|---|
| | LLCZ | LCZ | BFZ | KCZ | MCZ | CTZ |
| CBS601.85 | 0.00012 | 0.00024 | 0.031 | 0.031 | 0.063 | 0.13 |
| CBS200.88 | 0.00098 | 0.002 | 0.063 | 2 | 0.5 | 0.13 |
| CBS545.95 | 0.00098 | 0.00098 | 0.063 | 1 | 0.5 | 0.13 |
| CBS619.84 | 0.00098 | 0.002 | 0.13 | 2 | 0.5 | 0.25 |
| MIC range | 0.00012-0.00098 | 0.00024-0.002 | 0.031-0.13 | 0.031-2 | 0.063-0.5 | 0.13-0.25 |
| GM | 0.00058 | 0.00098 | 0.063 | 0.59 | 0.3 | 0.15 |

| clinical isolate | MIC (µg/mL) | | | | | |
|---|---|---|---|---|---|---|
| | ITZ | VCZ | FCZ | TBF | AMO | AMPB |
| CBS601.85 | 0.016 | 0.016 | 2 | 1 | 2 | 0.5 |
| CBS200.88 | >4 | 0.13 | >4 | 0.25 | 2 | 0.5 |
| CBS545.95 | >4 | 0.063 | >4 | 0.5 | 2 | 1 |
| CBS619.84 | >4 | 0.13 | >4 | 0.25 | 2 | 0.5 |
| MIC range | 0.016->4 | 0.016-0.13 | 2->4 | 0.25-1 | 2 | 0.5-1 |
| GM | >4 | 0.064 | >4 | 0.42 | 2 | 0.59 |

LLCZ: luliconazole,
LCZ: lanoconazole,
BFZ: bifonazole,
KCZ: ketoconazole,
MCZ: miconazole,
CTZ: clotrimazole,
ITZ: itraconazole,
VCZ: voriconazole,
FCZ: fluconazole,
TBF: terbinafine,
AMO: amorolfine,
AMPB: amphotericin B Industrial Applicability The antifungal agent of the present invention which contains luliconazole and/or lanoconazole as active ingredient(s) shows a high effect on *Scytalidium dimidiatum* and *Scytalidium hyalinum*, which are pathogenic fungi of superficial mycosis showing symptoms similar to those of tinea (misdiagnosed as tinea) in respective countries in the tropical (subtropical) areas such as Thailand and the like, North America and Europe in recent years, and is useful as a therapeutic agent for superficial mycosis.

This application is based on Japanese patent application No. 2011-209903, the contents of which are all encompassed in the present specification.

The invention claimed is:

1. A method of treating mycosis caused by a fungus of the genus *Scytalidium* as a pathogenic fungus, comprising administering an effective amount of luliconazole or a pharmaceutically acceptable salt thereof and/or lanoconazole or a pharmaceutically acceptable salt thereof to a subject.

2. The method according to claim 1, wherein the mycosis is superficial mycosis.

3. A method of treating complex mycosis caused by
   (1) a fungus of the genus *Scytalidium* and
   (2) one or more fungi selected from the group consisting of a fungus of the genus *Candida*, a fungus of the genus *Cryptococcus*, a fungus of the genus *Aspergillus*, a fungus of the genus *Trichophyton*, a fungus of the genus *Coccidioides*, a fungus of the Zygomycota, a fungus of the genus *Trichosporon*, a fungus of the genus *Microsporon*, a fungus of the genus *Scopulariopsis*, a fungus of the genus *Fusarium*, a fungus of the genus *Alternaria*, and a fungus of the genus *Acremonium*,
as pathogenic fungi, which comprises administering an effective amount of luliconazole or a pharmaceutically acceptable salt thereof and/or lanoconazole or a pharmaceutically acceptable salt thereof to a subject.

4. The method according to claim 3, wherein the complex mycosis is superficial mycosis.

5. The method according to claim 1, wherein the mycosis is selected from superficial mycosis, subcutaneous mycosis, deep mycosis, mycetoma, and fungemia.

6. The method according to claim 2, wherein the superficial mycosis is a mycosis developed by infection, with the pathogen, of the skin of leg, body and/or head, nail, eye, ear, mouth cavity, nasal cavity, respiratory organ, urinary tract, and/or vagina.

7. The method according to claim 1, wherein the fungus of the genus *Scytalidium* is *Scytalidium dimidiatum* and/or *Scytalidium hyalinum*.

8. The method according to claim 3, wherein the complex mycosis is selected from superficial mycosis, subcutaneous mycosis, deep mycosis, mycetoma, and fungemia.

9. The method according to claim 4, wherein the superficial mycosis is a mycosis developed by infection, with the pathogen, of the skin of leg, body and/or head, nail, eye, ear, mouth cavity, nasal cavity, respiratory organ, urinary tract, and/or vagina.

10. The method according to claim 3, wherein the fungus of the genus *Scytalidium* is *Scytalidium dimidiatum* and/or *Scytalidium hyalinum*.

* * * * *